(12) United States Patent
Breitling et al.

(10) Patent No.: US 6,387,627 B1
(45) Date of Patent: *May 14, 2002

(54) PHAGEMID FOR ANTIBODY SCREENING

(75) Inventors: Frank Breitling, Heidelberg; Melvyn Little, Neckargemund; Stefan Dübel, Dossenheim, all of (DE); Michael Braunagel, Oslo (NO); Iris Klewinghaus, Mannheim (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/645,436

(22) Filed: Aug. 25, 2000

Related U.S. Application Data

(62) Division of application No. 09/414,005, filed on Oct. 7, 1999, now Pat. No. 6,127,132, which is a division of application No. 09/135,002, filed on Aug. 17, 1998, now Pat. No. 5,985,588, which is a continuation of application No. 07/982,743, filed as application No. PCT/EP92/01524 on Jul. 6, 1992, now Pat. No. 5,849,500.

(30) Foreign Application Priority Data

Jul. 8, 1991 (DE) .......................................... 41 22 599

(51) Int. Cl.$^7$ .......................... C12Q 1/68; C12N 15/66; C12N 15/70; C12P 21/08; G01N 33/53
(52) U.S. Cl. .......................... 435/6; 435/7.1; 435/91.41; 435/320.1; 530/387.3
(58) Field of Search .......................... 435/320.1, 91.41, 435/7.1, 6; 530/387.1, 387.3

(56) References Cited

U.S. PATENT DOCUMENTS

| | | | |
|---|---|---|---|
| 5,849,500 A | * 12/1998 | Breitling et al. | 435/7.1 |
| 5,969,108 A | 10/1999 | McCafferty et al. | |
| 5,985,588 A | * 11/1999 | Breitling et al. | 435/7.8 |
| 6,127,132 A | * 10/2000 | Breitling et al. | 435/7.1 |
| 6,172,197 B1 | 1/2001 | McCafferty et al. | |

FOREIGN PATENT DOCUMENTS

WO    WO 9209690 A2    6/1992

OTHER PUBLICATIONS

McCafferty et al., Nature 348, pp. 552–554 (1990).
Ward et al., Nature 341, pp. 544–546 (1989).
Cwirla et al., Proc. Natl. Acad. Sci. USA 87, pp. 6378–6382 (1990).
Scott et al., Science 249, pp. 386–390 (1990).
Breitling et al., Gene 104, pp. 147–153 (1991).
Huse et al., Science 246, pp. 1275–1281(1989).
Day et al., Ann. Rev. Biophys. Chem. 17, pp. 509–539 (1988).
Smith et al., Science 228, pp. 1315–1317 (1985).
Parmley et al., Gene 73, pp. 305–318 (1988).
Devlin et al., Science 249, pp. 404–406 (1990).
Amit et al., Science 233, pp. 747–753 (1986).
Verhoeyen et al., Science 239, pp. 1534–1536 (1988).
Breitling et al., J. Mol. Biol. 189, 367–370 (1986).
Boss et al., Proteins: Structure, Function and Genetics, vol. 8, No. 4, Wiley Press, NY, US, pp. 309–314 (1990).
Bujard et al., Methods Enzymol 155, pp. 416–433 (1987).
Lanzer et al., Proc. Natl. Acad. Sci. USA 85, pp. 8973–8977 (1988).
Goldsmith et al., Biochemistry 16, pp. 2686–2694 (1977).
Boeke et al., Proc. Natl. Acad. Sci. USA 79, pp. 5200–5204 (1982).
Crissman et al., Virology 132, pp. 445–455 (1984).
Davis et al., J. Mol. Biol. 181, pp. 111–121 (1985).
Plackthun et al., J. Biol. Chem. 262, pp. 3951–3957 (1987).
Laemmli et al., Nature 227, pp. 680–685 (1970).
Towbin et al., Proc. Ntl. Acad. Sci. USA 76, pp. 4350–4354 (1979).
Webster et al., Structure and Assembly of the Class I Filamentous Bacteriophage, Duke University Medical Center, pp. 236–267 (1985).
Muller, H., PhD. thesis, Univ. of Heidelberg, cover sheets and pp. 56–58 (1989).
Sambrook et al., Molecular Cloning pp. 4.17–4.19 and 17.29–17.30 (1989).
Kang et al., Proc. Natl. Acad. Sci. USA, vol. 88 (1991) pp. 4363–1366.

\* cited by examiner

*Primary Examiner*—Terry McKelvey
(74) *Attorney, Agent, or Firm*—Birch, Stewart, Kolasch & Birch, LLP

(57) ABSTRACT

A phagemid has been constructed that expresses an antibody fused to coliphage pIII protein. The phagemid is suitable for selecting specific antibodies from large gene libraries with small quantities of antigen. The antibody-pIII gene can be strongly repressed, so that it allows antibody libraries to be amplified without the danger of deletion mutants predominating. After induction, large quantities of the fusion protein may be expressed.

8 Claims, 4 Drawing Sheets

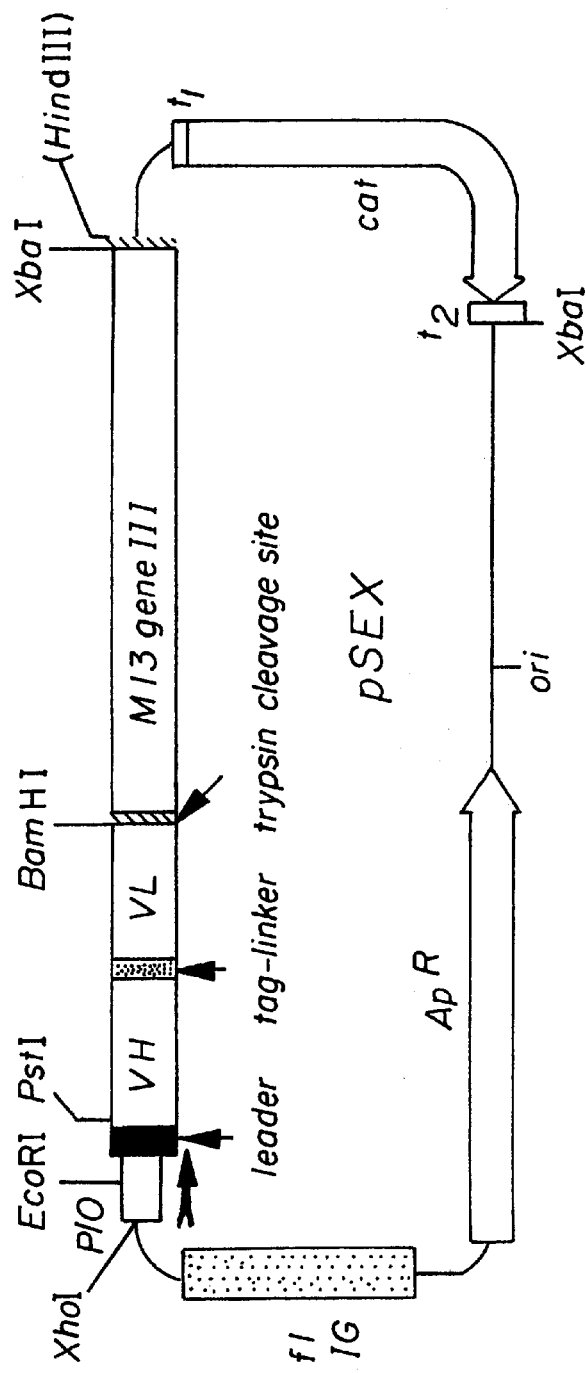

FIG. 1B

RBS　　　　　→ pelB leader
　　　　　　　MetLysTyrLeuLeuProThrAlaAlaAlaAlaGlyLeu
86
5'-GAATTCATTAAAGAGGAGAAATTAACTCCATGAAATACCTTGCCTACGGCAGCCGGCTTG
　EcoRI
　　　　　　　　　　　　　　　　(NcoI)

→ VH　　　　　　　　　523—tag-linker
　　　　　　　　　　　　　　　　　　　　　　　'SerSerGluGluGly
151
LeuLeuLeuAlaAlaAlaMetAlaGlnProAlaMetAlaGlnValGlnLeuGln...'SerSerGluGluGly
CTGCTGCTGGCAGCTGCAGCCGGCGATGGCGCAAGTTCAGCTGCAG...TCCTCAGAAGAAGGT
　　　　　　　　　　　　　　　　　　　　　　PstI → VL　　895
　　　　　　　　　　　　　　　　　　　　　'LysArgThr
538
GluPheSerGluAlaAlaArgGluAspMetAlaAlaAlaLeuGluLysGlyAspIle...'LysArgThr
GAATTCTCAGAAGCTCGTGAAGATATGGCTGCACTTGAGAAAGGTGATATC...AAACGTACG
　EcoRI　　　　　　　　　　　　　　　　　　　　　　EcoRV → M13 gene III
904
ValAlaAlaProGlySerLysAspIleArgAlaGluThrValGluSerCys...
GTAGCAGCTCCTGGATCCAAAGATATCAGAGCTGAAACTGTTGAAAGTTGT...
　　　　　　BamHI　　　EcoRV　　forward primer 2137
...ArgAsnLysGluSerStopStop
...CGTAATAAGGAGTCTTAATGACTCTAGAGTCAGCTT
...TTATTCCTCAGAATTACT XbaI (HindIII)
　backward primer

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (iii) HYPOTHETICAL: NO (v) FRAGMENT TYPE: N-terminal (ix) FEATURE:
      (A) NAME/KEY: Peptide
      (B) LOCATION: 1..10
      (D) OTHER INFORMATION: /label= peptide
         /note= "N-terminal sequence of heavy chain
         variable domain of scAb to hen egg white
         lysozyme."

(xi) SEQUENCE DESCRIPTION: SEQ ID NO:1:

Gln Val Gln Leu Gln Gln Ser Gly Gly Gly
1             5                  10

(2) INFORMATION FOR SEQ ID NO:2:

```
    (i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: N-terminal (ix) FEATURE:
        (A) NAME/KEY: Peptide
        (B) LOCATION: 1..10
        (D) OTHER INFORMATION: /label= peptide
              /note= "N-terminal sequence of light chain
              variable region of scAb to hen egg white lysozyme"

(xi) SEQUENCE DESCRIPTION: SEQ ID NO:2:

Asp Ile Gln Met Thr Gln Ser Pro Ser Ser
1               5                   10

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (A) NAME/KEY: -
        (B) LOCATION: 1..36
        (D) OTHER INFORMATION: /label= linker top strand (xi) SEQUENCE DESCRIPTION: SEQ ID NO:3:

GCTGAATTCG GATCCATAGG GCCCTCTAGA GTCGAC                                     36

(2) INFORMATION FOR SEQ ID NO:4:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..44
        (D) OTHER INFORMATION: /label= linker bottom strand (xi) SEQUENCE DESCRIPTION: SEQ ID NO:4:

AATTGTCGAC TCTAGAGGGC CCTATGGATC CGAATTCAGC TGCA                            44

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /label= linker
              /note= "top strand of linker encoding a
```

-continued protease-sensitive
       sequence"

(xi) SEQUENCE DESCRIPTION: SEQ ID NO:5:

GATCCAAAGA TATCAGAGGG CC                                          22

(2) INFORMATION FOR SEQ ID NO:6:

(i) SEQUENCE CHARACTERISTICS:
       (A) LENGTH: 14 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: -
       (B) LOCATION: 1..14
       (D) OTHER INFORMATION: /label= linker
           /note= "bottom strand of linker encoding
           protease-sensitive sequence"

(xi) SEQUENCE DESCRIPTION: SEQ ID NO:6:

CTCTGATATC TTTG                                                   14

(2) INFORMATION FOR SEQ ID NO:7:

(i) SEQUENCE CHARACTERISTICS:
       (A) LENGTH: 110 base pairs
       (B) TYPE: nucleic acid
       (C) STRANDEDNESS: both
       (D) TOPOLOGY: linear (ii) MOLECULE TYPE: DNA (ix) FEATURE:
       (A) NAME/KEY: -
       (B) LOCATION: 1..110
       (D) OTHER INFORMATION: /label= fragment
           /note= "EcoRI - PstI fragment of pSEX (nucleotides
           86 - 196), see Fig. 1"

(ix) FEATURE:
       (A) NAME/KEY: CDS
       (B) LOCATION: 30..110
       (D) OTHER INFORMATION: /product= "pelB leader sequence"

(xi) SEQUENCE DESCRIPTION: SEQ ID NO:7:

GAATTCATTA AAGAGGAGAA ATTAACTCC ATG AAA TAC CTC TTG CCT ACG GCA    53
                               Met Lys Tyr Leu Leu Pro Thr Ala
                                1               5

GCC GCT GGC TTG CTG CTG CTG GCA GCT CAG CCG GCG ATG GCG CAA GTT  101
Ala Ala Gly Leu Leu Leu Leu Ala Ala Gln Pro Ala Met Ala Gln Val
    10              15                  20

CAG CTG CAG                                                      110
Gln Leu Gln
 25

(2) INFORMATION FOR SEQ ID NO:8:

(i) SEQUENCE CHARACTERISTICS:
       (A) LENGTH: 27 amino acids
       (B) TYPE: amino acid
       (D) TOPOLOGY: linear (ii) MOLECULE TYPE: protein (xi) SEQUENCE DESCRIPTION: SEQ ID NO:8:

Met Lys Tyr Leu Leu Pro Thr Ala Ala Ala Gly Leu Leu Leu Leu Ala

```
                1               5              10              15
Ala Gln Pro Ala Met Ala Gln Val Gln Leu Gln
                       20              25
```

(2) INFORMATION FOR SEQ ID NO:9:

(i) SEQUENCE CHARACTERISTICS:
        (A) LENGTH: 66 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: -
        (B) LOCATION: 1..66
        (D) OTHER INFORMATION: /label= fragment
            /note= "tag-linker/scAb boundary in plasmid pSEX
            (nucleotides 523 - 589), see Fig. 1"

(ix) FEATURE:
        (A) NAME/KEY: CDS
        (B) LOCATION: 1..66

(xi) SEQUENCE DESCRIPTION: SEQ ID NO:9:

```
TCC TCA GAA GAA GGT GAA TTC TCA GAA GCT CGT GAA GAT ATG GCT GCA    48
Ser Ser Glu Glu Gly Glu Phe Ser Glu Ala Arg Glu Asp Met Ala Ala
 1               5                  10                  15
CTT GAG AAA GGT GAT ATC                                            66
Leu Glu Lys Gly Asp Ile
            20
```

(2) INFORMATION FOR SEQ ID NO:10:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:10:

```
Ser Ser Glu Glu Gly Glu Phe Ser Glu Ala Arg Glu Asp Met Ala Ala
 1               5                  10                  15
Leu Glu Lys Gly Asp Ile
            20
```

(2) INFORMATION FOR SEQ ID NO:11:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /label= fragment
            /note= "portion of pSEX plasmid (nucleotides 895
            -954) at scAb/gene III boundary, see Fig. 1"

(ix) FEATURE:
        (A) NAME/KEY: CDS
        (B) LOCATION: 1..60

(xi) SEQUENCE DESCRIPTION: SEQ ID NO:11:

```
AAA CGT ACG GTA GCA GCT CCT GGA TCC AAA GAT ATC AGA GCT GAA ACT        48
Lys Arg Thr Val Ala Ala Pro Gly Ser Lys Asp Ile Arg Ala Glu Thr
 1               5                  10                  15

GTT GAA AGT TGT                                                        60
Val Glu Ser Cys
             20
```

(2) INFORMATION FOR SEQ ID NO:12:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:12:

```
Lys Arg Thr Val Ala Ala Pro Gly Ser Lys Asp Ile Arg Ala Glu Thr
 1               5                  10                  15

Val Glu Ser Cys
             20
```

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: -
        (B) LOCATION: 1..36
        (D) OTHER INFORMATION: /label= fragment
            /note= "end of fusion protein-encoding insert in
            pSEX (nucleotides 2137 to HindIII site), see Fig.
            1"

(ix) FEATURE:
        (A) NAME/KEY: CDS
        (B) LOCATION: 1..15
        (D) OTHER INFORMATION: /product= "end of gene III portion
            of scAb/gene III fusion protein"

(xi) SEQUENCE DESCRIPTION: SEQ ID NO:13:

```
CGT AAT AAG GAG TCT TAATGACTCT AGAGTCAGCT T                            36
Arg Asn Lys Glu Ser
 1               5
```

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:14:

```
Arg Asn Lys Glu Ser
 1               5
```

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single -continued

```
            (D) TOPOLOGY: linear (ii) MOLECULE TYPE: DNA (ix) FEATURE:
            (A) NAME/KEY: -
            (B) LOCATION: 1..18
            (D) OTHER INFORMATION: /label= primer
                /note= "backward primer, see Fig. 1"

(xi) SEQUENCE DESCRIPTION: SEQ ID NO:15:

TCATTAAGAC TCCTTATT                                                 18

(2) INFORMATION FOR SEQ ID NO:16:

(i) SEQUENCE CHARACTERISTICS:
            (A) LENGTH: 63 base pairs
            (B) TYPE: nucleic acid
            (C) STRANDEDNESS: both
            (D) TOPOLOGY: linear (ii) MOLECULE TYPE: DNA (ix) FEATURE:
            (A) NAME/KEY: -
            (B) LOCATION: 1..63
            (D) OTHER INFORMATION: /label= linker
                /note= "alternative tag-linker sequence, see Fig.
                1(c)"

(ix) FEATURE:
            (A) NAME/KEY: CDS
            (B) LOCATION: 1..63

(xi) SEQUENCE DESCRIPTION: SEQ ID NO:16:

TCA GGG AGT GCA TCC GCC CCA AAG CTT GAA GAA GGT GAA TTC TCA GAA     48
Ser Gly Ser Ala Ser Ala Pro Lys Leu Glu Glu Gly Glu Phe Ser Glu
 1               5                  10                  15

GCG CGC GAA GAT ATC                                                 63
Ala Arg Glu Asp Ile
            20

(2) INFORMATION FOR SEQ ID NO:17:

(i) SEQUENCE CHARACTERISTICS:
            (A) LENGTH: 21 amino acids
            (B) TYPE: amino acid
            (D) TOPOLOGY: linear (ii) MOLECULE TYPE: protein (xi) SEQUENCE DESCRIPTION: SEQ ID NO:17:

Ser Gly Ser Ala Ser Ala Pro Lys Leu Glu Glu Gly Glu Phe Ser Glu
 1               5                  10                  15

Ala Arg Glu Asp Ile
            20
```

PHAGEMID FOR ANTIBODY SCREENING

This application is a divisional of application Ser. No. 09/414,005, filed on Oct. 7, 1999, now U.S. Pat. No. 6,127,132, which is a divisional application of application Ser. No. 09/135,002, filed Aug. 17, 1998, now U.S. Pat. No. 5,985,588, which is a continuation application of application Ser. No. 07/982,743 filed on May 10, 1993, now U.S. Pat. No. 5,849,500 which is the national phase of PCT International Application No. PCT/EP92/01524 filed on Jul. 6, 1992 under 35 U.S.C. § 371. The entire contents of each of the above-identified applications are hereby incorporated by reference.

The present invention concerns phagemids for the selection of specific antibodies from large recombinant libraries, the production of these phagemids and their use to select specific antibodies from large recombinant libraries using small amounts of antigen.

Plasmid and phage antibody libraries have been established in *E. coli* from PCR amplified immunoglobulin families following immunization. Recombinant antibodies to immunogens were selected by an ELISA assay of the bacterial supernatant from isolated bacterial colonies (Ward, E. S., Güssow, D., Griffiths, A. D., Jones, P. T. & Winter, G.: Binding activities of a repertoire of single immunoglobulin variable domains secreted from *Escherichia coli*. Nature 341 (1989) 544–546) or by screening nitrocellulose plaque lift-offs of bacterial colonies for reactivity to the radioactively labeled immunogen (Huse, W. D., Sastry, L., Iverson, S. A., Kang, A. S., Alting-Mees, M., Burton, D. R., Benkovic, S. J. and Lerner, R. A.: Generation of a large combinatorial library of the immunoglobin repertoire in phage lambda. Science 246 (1989) 1275–1281). However, for the selection of specific antibodies from randomly combined light and heavy chain libraries of non-immunized animals that do not contain a preponderance of antibodies to a particular antigen, a procedure is required for screening millions of antibody producing bacteria.

A possible way to screen a broad range of antibodies is to attach recombinant antibodies to the surface of bacteria or bacteriophages so that they can then be rapidly selected by antigens bound to a solid phase. Given the difficulties of targeting proteins to the cell surface of bacteria, an attractive candidate in view of its small size and relatively simple genetic make-up is the M13 family of filamentous bacteriophages (for reviews see Webster, R. E. and Lopez, J. in "Virus Structure and Assembly" ed. S. Casjens, publ. Jones and Bartlett Inc., Boston/Portala Valley, USA, 1985; Day, L. A., Marzec, C. J., Reisberg, S. A. and Casadevall, A.: DNA packaging in filamentous bacteriophages. Ann. Rev. Biophys. Biophys. Chem. 17 (1988) 509–539).

The product of gene III (pIII) is a relatively flexible and accessible molecule composed of two functional domains; an amino-terminal domain that binds to the F pilus of male bacteria during infection and a carboxy-terminal domain buried within the virion that is important for morphogenesis. Peptides can be inserted between the two domains of pIII (Smith, G. P.: Filamentous fusion phage: novel expression vectors that display cloned antigens on the virion surface. Science 228 (1985) 1315–1317) or near the N-terminus (Parmley, S. F. and Smith, G. P.: Antibody-selectable filamentous fd phage vectors: affinity purification of target genes. Gene, 73 (1988) 305–318) without destroying its functions in morphogenesis and infection. After much pioneering work on the use of pIII in fd phages for carrying foreign peptides, Parmely and Smith (1988, a.a.O.) showed that peptide epitopes inserted at the aminoterminal end could bind phages to immobilized antibodies. As a consequence of this work it has been possible to generate peptide libraries that can be screened for binding to ligands and antibodies (Scott, J. K. and Smith, G. P.: Searching for peptide ligands with an epitope library. Science 249 (1990) 386–390; Devlin, J. J., Panganiban, L. C. and Devlin, P. E.: Random peptide libraries: A source of specific protein binding molecules. Science 249 (1990) 404–406; Cwirla, S. E., Peters. E. A., Barrett, R. W. and Dower, W. J. Peptides on phage, a vast library of peptides for identifying ligands.: Proc. Natl. Acad. Sci. USA, 87 (1990) 6378–6382).

McCafferty, J., Griffiths, A. D., Winter, G. and Chiswell, D. J.: Phage antibodies: filamentous phage displaying antibody variable domains. Nature, 348 (1990) 552–554 reported the assembly of an antibody-pIII fusion protein into an fd phage with a $Tet^R$ gene after inserting antibody DNA into the 5' end of gene III. The phage remained infectious and was able to be enriched by affinity chromatography. However, fusion phage have been shown to be mainly useful for displaying relatively small inserts, probably, because the large inserts have an adverse effect on the infectivity function of pIII (Parmlee and Smith, 1988, a.a.O). There is a large risk, therefore, that phage libraries will quickly become dominated by deletion mutants after library amplification.

Thus the technical problem underlying the present invention is to provide a more efficient mean for screening antibody libraries in bacteria.

This problem is solved by providing a phagemid according to claim 1 that expresses a functional antibody-pIII fusion protein. Preferably the antibody is a single-chain antibody. DNA coding for an antibody-pIII fusion protein, preferably a single-chain antibody-pIII fusion protein, was incorporated into a phagemid. A major advantage of the phagemid system of this invention over McCafferty et al. (see above) is that it can be propagated as a plasmid and is not under any selection pressure to remove antibody DNA, since the expression of the fusion protein is tightly repressed. This is particularly important during the amplification of antibody libraries when faster proliferating deletion mutants could quickly dominate. The phagemid DNA, being less than half the size of the above phage DNA, also transform bacteria more efficiently. Moreover, in contrast to the above mentioned phage system, large quantities of the smaller phagemid DNA are produced and large amounts of antibody protein are available after induction, thereby greatly facilitating its analysis.

Expression of the antibody-pIII fusion protein, preferably the single-chain antibody-pIII fusion protein, using the pSEX phagemid (see below) and its packaging into viral particles greatly facilitate the establishment of bacterial systems for the isolation of high affinity antibodies. Millions of antibody-producing clones from antibody libraries can now be rapidly screened by binding to immobilized antigen. A further advantage over conventional screening methods is that only small amounts of antigen are required, an important factor when the supply of a rare protein is limited. This system also offers the possibility of screening randomly mutated antibodies in order to increase their binding affinities. The procedure could be repeated many times until the desired specificity is achieved. It is now feasible for the first time to carry out large scale differential screening analyses of related cells and organisms. A substractive selection, e.g., using normal and neoplastic cells could be used to identify tumor associated antigens. The phagemid system also proves to be extremely useful for investigating the component,of molecular interactions e.g. by selecting antibodies that inhibit ligand receptor binding.

Furthermore, the system of this invention is mostly useful for presenting other proteins or peptides at the surfaces of phagemid viral particles. For this purpose the DNA encoding the antibody has to be replaced with DNA of the desired polypeptide.

BRIEF DESCRIPTION OF THE DRAWINGS

FIG. 1A is a restriction map of the phagemid pSEX.

FIG. 1B (SEQ ID NOS:7–15) describes the ribosome binding site (RBS), leader sequence of pectate lyase, tag linker and the PCR primers for pIII.

FIG. 1C (SEQ ID NOS:16–17) describes an alternative taglinker sequence.

The following Examples illustrate but not restrict the present invention.

EXAMPLES

Example 1
Construction of phagemid (pSEX)

DNA coding for a single chain antibody (scAb) and pIII were cloned into pUC119 after insertion of a specific set of restriction sites and a protease sensitive joining sequence into the multiple cloning site. The Ab-DNA coded for the heavy and light chain variable domains of a humanised Ab against hen egg white lysozyme derived from the anti-lysozyme Ab D1.3 (Amit et al., Science 233, p. 747–754, 1986; Verhoeyen, M. et al. Science 239 p. 1534–1536, 1988). These domains were joined by an eighteen amino acid linker sequence containing the epitope for the monoclonal Ab YOL1/34 (Breitling, F. and Little, M.: Carboxy-terminal regions on the surface of tubulin and microtubules. Epitope locations of YOL1/34, DM1A and DM1B. J. Mol. Biol. 189 (1986), 367–370), thus enabling the Ab to be identified. To provide a more flexible junction to pIII, the 3' end of the light chain DNA was modified by the addition of nucleotides coding for the first six amino acids of the human kappa constant domain followed by a BamHI restriction site. pIII DNA was amplified from the bacteriophage M13 using primers corresponding to the 5' and 3' ends of gene III. The Ab-pIII-DNA was then cloned into a phagemid of the pDS family that contains a coliphage T7 promoter combined with two lac operators (Bujard, H., Gentz, R., Lancer, M., Stüber, D., Müller, H.-M., Ibrahim, I., Häuptle, M.-T. and Dobberstein, B.: A T5 promoter-based transcription-translation system for the analysis of proteins in vitro and in vivo. Methods Enzymol. 155 (1987) 416–433; Lancer, M. and Bujard, H.: Promoters determine the efficiency of repressor action. Proc. Natl. Acad. Sci. USA 85 (1988) 8973–8977); Müller, H.-M. Ph.D thesis, Univ. of Heidelberg, 1989). In a final step, DNA coding for the leader sequence of the bacterial enzyme pectate lyase was ligated to the 5' end of the Ab-DNA resulting in the phagemid pSEX (FIG. 1a). The leader, linker and PCR primer sequences are shown in FIG. 1b. An alternative linker sequence (FIG. 1c) with the YOL1/34 epitope placed at the end of the linker containing a useful restriction site for the insertion of Ab libraries was also employed. Although both of these tag-linkers contain a significant number of acidic residues, they appeared to have no effect on the production of functional scAbs when compared to scAbs with linkers composed only of the neutral amino acids glycine and serine.

Example 2
Expression of antibody-pIII fusion protein

Figures 2A, 2B:
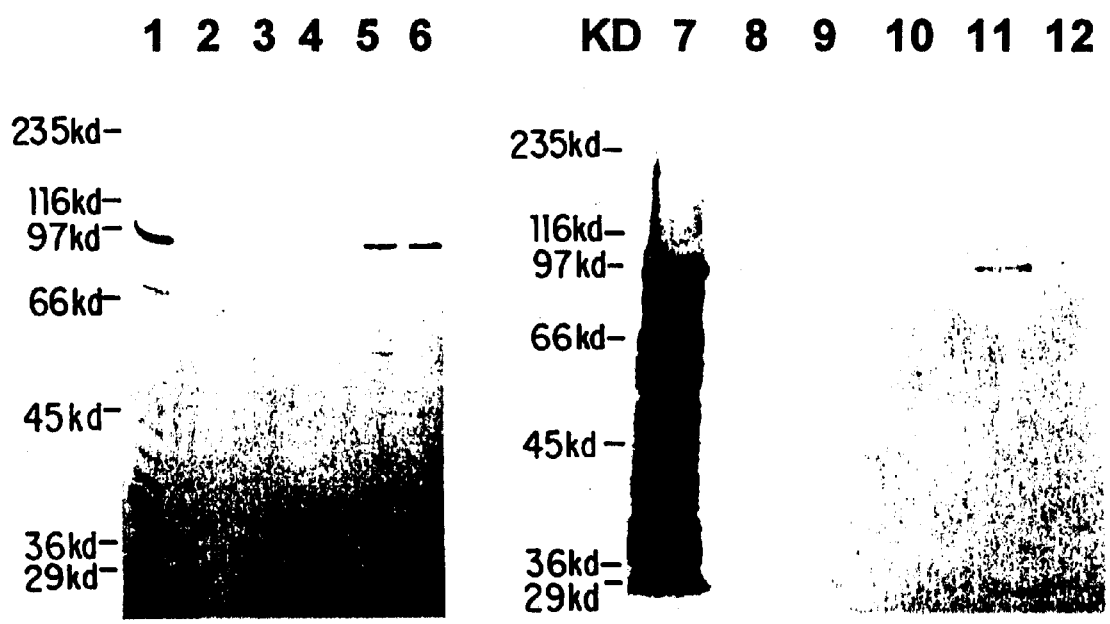
FIGS. 2A–2B show the results of a Western blot analysis for identification of the antibody-pIII fusion protein.

To test whether the completed phagemid vector was able to express the full length fusion protein, 100 μM IPTG was added to a log phase culture of E. coli transformed with pSEX. The culture showed a marked decline in its rate of growth compared to the control indicating a significant synthesis of phagemid encoded protein. On Western blot analysis, the antibody-pIII construct was identified by three antibodies; a monoclonal antibody to part of the linker sequence (EEGEFSEAR) (SEQ ID NO:10, residues 3–11) and two antipeptide rabbit sera against N-terminal sequences of the heavy (SEQ ID NO:1) and light chains (QVQLQQSGGG and DIQMTQSPSS (SEQ ID NO:2), respectively). It migrated with an apparent molecular weight of 93 kd (FIG. 2). The large size of the fusion protein (predicted: Mr 68100) is most probably due to the pIII component (Mr 42100) that migrates with an apparent molecular weight of approximately 55000–70000 kd (Goldsmith, M. E. and Konigsberg, W. H.: Adsorption protein of the bacteriophage fd: isolation, molecular properties and location in the virus. Biochemistry, 16 (1977) 2686–2694). Partial proteolysis of the fusion protein was indicated by the presence of some minor bands of lower molecular weight that were identically stained by all three antibodies.

Cell fractionation showed that the protein was present in the cytoplasmic and membrane fractions but not in the periplasm and culture supernatant (FIG. 2, lanes 3–6) in contrast to the antibody component alone without pIII that was secreted into the periplasm and medium (data not shown). This was not surprising since pIII is assembled onto phage particles from the inner bacterial membrane, a process that appears to be dependent only on the C-terminal domain. Deletion mutants of pIII without this domain pass into the periplasm without becoming attached to the cytoplasmic membrane (Boeke, J. D. and Model, P.: A prokaryotic membrane anchor sequence: carboxyl terminus of bacteriophage f1 gene III protein retained in the membrane. Proc. Natl. Acad. Sci. USA 79 (1992) 5200–5204) and normal phage particles are not assembled (Crissman, J. W. and Smith, G. P.: Gene III protein of filamentous phages: evidence for a carboxy-terminal domain with a role in morphogenesis.: Virology, 132 (1984) 445–455). The anchor sequence is probably a hydrophobic stretch of twenty three amino acids at the carboxy-terminus (Davis, N. G., Boeke, S. and Model, P.: Fine structure of a membrane anchor domain. J. Mol. Biol. 181 (1985) 111–121).

The ability of the fusion protein to bind antigen was investigated by passing the triton soluble fraction over a column of lysozyme bound to sepharose. Western blots of the unbound material and the fractions obtained after thoroughly washing and eluting with 0.05 M diethylamine showed that the full length fusion protein was indeed specifically retained on the lysozyme column (FIG. 2, lanes 7–12).

Example 3
Packaging of the pSEX phagemid

Figure 3:
FIG. 3 shows the results of gel electrophoresis of circular single stranded pSEX.

To determine whether the phagemid expression vector could be packaged, E. coli containing pSEX were multiply infected with phage fd. IPTG was not added since it was found to have an inhibitory effect on phagemid packaging. A similar finding was recently reported by Bass et al., Proteins 8, S. 309–314 (1990) who constructed a phagemid that expresses a fusion protein of human growth hormone and the C-terminal domain of pIII. Examination of Ab-pIII production with and without IPTG after adding phage fd showed that the phage alone was able to induce expression (FIG. 3). A possible explanation is that one of the phage gene products interferes with the binding of lac repressor to the operator. Alternatively, phage proteins binding to the intergenic region might affect the topology of the phagemid and cause the release of the lac repressor; Whatever the reason, we have found that moving the intergenic region $10^3$ nucleotides to the other side of the bla gene has no effect on this phenomenon (data not shown).

Agarose gel electrophoresis of the DNA from virus particles secreted into the medium showed, in addition to the single stranded DNA of fd, a larger quantity of smaller DNA that was compatible in size with single stranded pSEX. Further proof of phagemid packaging and the production of infectious particles was shown by infecting $E.coli$ with the secreted virus particles. $10^{10}$/ml AmpR colonies of $E.coli$ were obtained in comparison to $3 \times 10^9$ pfu.

To determine whether the packaged phagemid had incorporated the antibody-pIII fusion protein, 90 µl culture supernatant containing $5 \times 10^8$ packaged phagemids determined as $Amp^R$ transducing units was mixed with a 1000-fold excess of wild type fd phage and passed over a column of immobilized lysozyme. After thoroughly washing with ten bed volumes of PBS, 1M NaCl and 0.5 M NaCl in 0.1 M $NaHCO_3$ at pH 8.3, respectively, the phagemid particles were eluted with 0.05 M diethylamine. The eluate was neutralized with 0.5 M $NaH_2PO_4$ and assayed for the number of phages and packaged phagemids (Table). A specific enrichment of up to 121-fold was achieved, thus demonstrating the incorporation of functional antibody-pIII constructs into phagemid particles. The binding properties of the phagemid particles might be further increased by using a pIII deletion mutant for packaging. This would ensure that only those phagemids coding for functional fusion proteins would be packaged and all five pIII proteins on a phagemid particle would be fused to antibodies.

Description of the Figures

FIG. 1 Construction of pSEX, a phagemid for antibody screening

VH and VL are heavy and light chain variable domains, respectively, of an anti-lysozyme Ab.

a) Construction.

To provide the necessary restriction sites, the oligonucleotides 5'GCTGAATTCGGATCCATAGGGCCCTCTA-GAGTCGAC3' (SEQ ID NO:3) and 5'AATTGTC-GACTCTAGAGGGCCCTATGGATCCGAATTCAGCTGCA3' (SEQ ID NO:4) were 5' phosphorylated, hybridized and ligated to pUC119 that had been cleaved with PstI and EcoRI and dephosphorylated. In an optional step to create a protease sensitive sequence, the hybridized oligonucleotides 5'GATCCAAAGATATCAGAGGGCC3' (SEQ ID NO:5) and 5'CTCTGATATCTTTG3' (SEQ ID NO:6) were inserted between the BamHI and ApaI sites of the first set of oligonucleotides. scAB-DNA was then inserted between the PstI and BamHI followed by the blunt end ligation of pIII DNA after cleaving the phagemid with ApaI and treating with T4 DNA polymerase to remove 3' overhanging ends. pSEX was constructed by combining the multiple cloning site of pUHE24-2 with the closely related phagemid pDS31-1 that contains an additional f1 intergenic region (Bujard et al., 1987, see above,; Müller, 1989, see above). The pDS31-1 sequence extends from Xho1 anticlockwise to a HindIII site (in parentheses) that was lost after a blunt end ligation. pUHE24-2 is essentially identical to pDS6 (Bujard et al., 1987) with a coliphage T7 promoter combined with two lac operators and a ribosome binding site (PA1/04/03, Lancer and Bujard, 1988, see above; Lanzer, 1988, see above). The resulting phagemid was cleaved with HindIII and the 5'overhangig ends were filled up with Klenow fragment. After a further digestion with PstI, the PstI-HincII Ab-pIII-DNA fragment was inserted into the phagemid. In a final step, synthetic DNA coding for the leader sequence of the bacterial enzyme pectate lyase and for the first four amino acids of the heavy chain was inserted between the NcoI and PstI restriction sites. pUHE plasmids were propagated in $E.coli$ 71-18 with the plasmid pDM1 that expresses lac repressor, pUC plasmids were propagated DH5α and the antibody-pIII fusion protein was expressed in TM101.

b) Sequence of the ribosome binding site (RBS), leader sequence of pectate lyase, tag-linker and the PCR primers for pIII.

Underlined amino acids indicate the epitope for YOL1/34. The following amino acids in the linker sequence are a continuation of the α-tubulin sequence (SEQ ID NO:7-15).

c) Alternative tag-linker sequence. Underlined amino acids indicate the epitope for YOL1/34. The preceding linker amino acids are a continuation of Ab sequence into the constant domain (SEQ ID NO:16).

FIG. 2 Inducibility, cellular localization and antigen binding of the antibody-pIII fusion protein analyzed by gel electrophoresis on 8% poly-acrylamide gels and Western blotting Lanes 1 and 2: Total cells after 1 h induction with 100 µM IPTG (1) or without IPTG (2). Lanes 3–6: Cell fractionation; 3: culture supernatant, 4: periplasmic enriched fraction, 5: soluble cytoplasmic fraction, 6: 1% triton extract. Lanes 7–12: Lysozyme affinity chromatography of the 1% triton extract from induced and non-induced cells, 7: effluent (+IPTG), 8: effluent (–IPTG), 9: last wash (+IPTG), 10: last wash (–IPTG), 11: eluate (+IPTG), 12: eluate (–IPTG).

Lanes 1–6 were stained using the monoclonal antibody YOL1/34 (Serotec, Oxford, U.K.) and lanes 7–12 using an antiserum to the N-terminal sequence of the light chain.

Method:

Antisera to the heavy and light chains were obtained by the subcutaneous injection of rabbits with the amino-terminal peptides QVQLQQSGGG (AC) (SEQ ID NO:1) and DIQMTQSPSS (AC) (SEQ ID NO:2), respectively, coupled to keyhole limpet heamocyanin. To investigate the expression of the fusion protein, the pelleted bacteria of IPTG-induced cultures were resuspended in 30 mM Tris/HCl, pH 8.0 containing 20% sucrose. 1 mM EDTA, 1 mg/ml chick lysozyme and incubated for 10 min on ice. After centrifuging for 1 min at 15000 g, the supernatant containing the periplasmic proteins was collected and the pellet was sonicated in 0.1 M Tris/HCl pH 8.0. The soluble cytosolic fraction was decanted after centrifuging for 5 min at 15000 g and the resuspended pellet was incubated in 1% Triton X100 to obtain the membrane bound fraction. All the fractions were analyzed for β-lactamase activity according to Plückthun, A. and Knowles, J. R.: The consequences of stepwise deletions from the signal-processing site for β-lactamase. J. Biol. Chem. 262 (1987) 3951–3957 to check the efficiency of the fractionation procedure. The triton soluble fraction was diluted a 100-fold with PBS before applying to affinity columns. For affinity chromatography, chick lysozyme (Boehringer, Mannheim, FRG) was coupled to cyanogen bromide activated Sepharose (Pharmacia) according to the instructions of the manufacturer. The lysozyme-Sepharose was incubated for 20 min at room temperature with the extracts and poured into columns that were subsequently washed with ten bed volumes of PBS, 1M NaCl and 0.5M in 0.1M $NaHCO_3$ at pH 8.3, respectively, before eluting with 0.05M diethylamine. All the fractions were precipitated with trichloracetic acid (final concentration 20%) and resolved on SDS polyacrylamide gels (Laemmli, U.K.: Cleavage of structural proteins during the assembly of the head of the bacteriophage T4. Nature 227 (1970) 680–685). Western blots were performed according to Towbin, H. Staehelin, T. and Gordon, I.: Electrophoretic transfer of protein from polyacrylamide gels to nitro-cellulose sheets: procedures and some applications (1979), Proc. Natl. Acad. Sci. USA 76, 4350–4354, using second antibodies coupled to horseradish peroxidase with diaminobenzidene as substrate.

FIG. 3 Gel electrophoresis of circular single stranded pSEX

Lane 1: fd, lane 2: control phagemid pUHE31-1 with fd, lane 3: pSEX1 with fd.

DNA from fd virions and packaged phagemid particles was applied to 0.8% agarose gels in 1×TBE according to Sambrook, J., Fritsch, E. F. and Maniatis, T. in Molecular Cloning: A Laboratory Manual, 2nd. ed. Cold Spring Harbor Laboratory (1989) and stained with ethidium bromide.

Method:

For the preparation of packaged phagemids, *E. coli* JM101 containing pSEX1 was plated onto M9 minimal medium and incubated for 30 h at 37° C. 2 ml of the same medium was inoculated with one of the colonies and incubated at 37° C. with vigorous aeration until it reached an optical density of about 0.2 at 600 nm. 0.5 ml of LB medium and a 10-fold excess of phage fd were then added to the culture and it was incubated for a further 3 h at 37° C. After carefully centrifuging twice at 15000 g for 5 min at room temperature, the supernatant was adjusted to a final concentration of 4% polyethylene glycol (Serva PEG 6000) and 0.5M NaCl and left to stand overnight at 4° C. The phagemids were sedimented by centrifuging at 15000 g for 20 min at room temperature and suspended in 200 $\mu$l of a Tris-EDTA buffer, pH 7.5. Phagemid DNA was prepared by shaking with one volume of phenol for ten minutes followed by treatment with chloroform-isopro-panol and precipitated with isopropanol (Sambrook, J., Fritsch, E. F. and Maniatis, T. in Molecular Cloning: A Laboratory Manual, 2nd. ed. Cold Spring Harbor Laboratory (1989)).

TABLE

| | | Specific enrichment of packaged phagemids on an antigen affinity colum | | | | | | |
|---|---|---|---|---|---|---|---|---|
| | | Amp$^r$ Colonies | | | Total pfu | | | |
| | Total Volume (ml) | Plated Volume ($\mu$l) | Number | Total | Plated Volume ($\mu$l) | Number | Total | Excess pfu/Amp$^r$ | Enrichment Factor |
| Applied | 10 | $10^{-3}$ | 51 | $5.1 \times 10^8$ | $10^{-6}$ | 45 | $4.5 \times 10^{11}$ | 882 | — |
| Eluted | 1.1 | $10^{-1}$ | 26 | $2.9 \times 10^5$ | $10^{-2}$ | 19 | $2.1 \times 10^6$ | 7.3 | 121 |

We claim:

1. A phagemid comprising DNA encoding a polypeptide-coliphage pIII fusion protein, wherein said fusion protein comprises an antibody polypeptide and a coliphage pIII polypeptide and wherein said coliphage pIII polypeptide comprises contiguous amino and carboxy domains of a coliphage pIII protein.

2. A phagemid according to claim 1 wherein the antibody polypeptide is a single chain antibody polypeptide.

3. A phagemid according to claim 1 or claim 2 wherein said polypeptide-coliphage pIII fusion protein contains a protease-sensitive region between the antibody polypeptide and the coliphage pIII polypeptide.

4. A phagemid according to claim 3 wherein said phagemid further comprises expression control elements upstream of said DNA and further encodes at least one selectable marker.

5. A process for the production of a phagemid according to claim 1, comprising the step of incorporating the DNA encoding said polypeptide-coliphage pIII fusion protein into a phagemid vector.

6. A library of phagemids wherein said phagemids are as defined in any one of claims 1 to 2 and wherein said phagemid library contains a plurality of members having different antibody polypeptides.

7. A method of selecting antibodies from a library according to claim 6, comprising screening said library with an antigen.

8. A method according to claim 7 further comprising the production of an antibody to said antigen identified following said screening of said library.

* * * * *